United States Patent [19]

Scanlon

[11] Patent Number: 5,736,326
[45] Date of Patent: Apr. 7, 1998

[54] METHOD OF DETECTING RESISTANCE TO CHEMO THERAPEUTIC AGENTS IN CANCER PATIENTS

[75] Inventor: Kevin J. Scanlon, Pasadena, Calif.

[73] Assignee: City of Hope, Duarte, Calif.

[21] Appl. No.: 299,332

[22] Filed: Aug. 31, 1994

Related U.S. Application Data

[63] Continuation of Ser. No. 234,096, Aug. 19, 1988, abandoned, which is a continuation-in-part of Ser. No. 46,127, May 5, 1987, abandoned.

[51] Int. Cl.$^6$ .............................. C12P 19/34; C12Q 1/68
[52] U.S. Cl. .............................. 435/6; 435/91.2; 935/77; 935/78
[58] Field of Search .................. 435/6, 91.2; 935/77, 935/78

[56] References Cited

U.S. PATENT DOCUMENTS 4,683,195  7/1987  Mullis ........................................... 435/6

OTHER PUBLICATIONS

Alt, et al., *J.Biol.Chem.* 253:1357–1370 (1978).
Stark, *Cancer Surveys*, 5:1–23 (1986).
Kraker, et al., *Cancer Lett*, 38:307–314 (1988).
Jenh, et al., *Molecular Pharmacology* 28:80–85 (1985).
Schimke, et al., *Science* 202:1051–1055 (1978).
Bertino, et al., *Proc.5thInt.Cong.Pharmacology* 3:376–392 (1972).
Scanlon, et al., *Proc.Natl'l.Acad.Sci.* 85:650 (1988).
Welch, *Cancer Research* 19:359–371 (1959).
Bertino, et al., *27th Annual Symposium on Fundamental Cancer Research*, pp. 681–689 (1975).
Bertino, *Cancer Res.* 39:293–304 (1979).
Miller, et al., *J.Biol.Chem.* 257:10204–10209 (1982).
Stark, et al., *Ann.Rev.biochem.* 53:447–491 (1984).
Chen., et al., *Cell* 47:381–389 (1986).
Beck, *Biochem.Pharmacology* 36:2879–2887 (1987).
Fojo, et al., *J.Clin.Oncology* 5:1922–1927 (1987).
Schimke, *J.Biol.Chem.* 263:5989–5992 (1988).
Croop, et al., *J.Clin.Invest.* 81:1303–1309 (1988).
Sklar, *Cancer.Res.* 48:793–797 (1988).
Scanlon, K.J., Kashani–Sabet, M., Tone, T., Funato, T., "Cisplatin Resistance in Human Cancers", Biochemical Pharmacology, Department of Medical Oncology, City of Hope, Duarte, California (Nov. 12, 1991).
Fairchild et al., Cancer Res. 47:5141–5148 (Oct. 1, 1987).
Marx, S. Science 223 pp. 40–41, 1984.
Guilotto, et al Cell vol. 48, 837 845, 1987.

*Primary Examiner*—Stephanie W. Zitomer
*Attorney, Agent, or Firm*—Rothwell, Figg, Ernst & Kurz

[57] ABSTRACT

This invention provides a process for detecting acquired resistance to any chemotherapeutic agent by any type of human cancer cell. The process comprises assaying RNA from human cancer cells to determine whether the expression of at least one of a preselected spectrum of least two different genes is increased in comparison to a control.

14 Claims, 18 Drawing Sheets m - RNA expression in colon cells sensitive and resistant to cisplatin a. DHFR b. TS c. TK Analysis of DNA from colon cells sensitive and resistant to cisplatin b. Southern

METHOD OF DETECTING RESISTANCE TO CHEMO THERAPEUTIC AGENTS IN CANCER PATIENTS

This application is a continuation of Ser. No. 07/234,096 filed Aug. 19, 1988, now abandoned, which is a continuation-in-part of application Ser. No. 07/046,127 filed May 5, 1987, now abandoned.

FIELD OF THE INVENTION

This invention relates to the detection of acquired cancer patient resistance to chemotherapeutic agents. More particularly the invention relates to phenomena indicative of acquired resistance which implicate a spectrum of genes, to assays useful to identify and quantify such phenomena and to cancer therapy regimens instructed by such phenomena.

BACKGROUND OF THE INVENTION

DNA amplification to permit survival of cells exposed to an inhibitor is ubiquitous.[1] It has been shown to be responsible for patient resistance to some drugs. The dihydrofolate reductase gene (DHFR) is amplified in tumor cells taken from patients treated with methotrexate. Amplification of the multidrug resistance gene (MDR) is a concomitant of acquired human tumor resistance to a plurality of drugs. The activity of DNA polymerase β, an enzyme involved in the repair of DNA damage, was elevated in P388 murine leukemia cell line resistant to ciplatinum.[2] The thymidylate synthase gene is amplified in murine cell lines resistant to fluorodeoxyuridine.[3] Asparate transcarbamylase amplification has been shown to evidence resistance to N-phosphonacetyl-L-aspartate (PALA).[4] Amplification of cytidine deaminase occurs as cells become resistant to ara-C and amplification of asparagine synthetase is demonstrated by cells resistant to L-asparaginase.[5]

[1] See generally (1986) Stark, G. R. *Cancer Surveys* 1–9.
[2] (1988) Kraker et al. *Cancer Lett.* 38:307–314.
[3] (1985) Jehn, et al. *Molecular Pharmacology* 28:80–85.
[4] (1978) Schimke, *Science* 202:1054.
[5] (1973) Bertino, et al., *Proc. 5th Int. Congr. Pharmacology* 3:376–392.

Heretofore the art has focused upon correlation of gene amplification with the acquired resistance of specific tumors to particular drugs. There is no known prior art teaching of the substantially concurrent analyses of a spectrum of genes to provide data indicative of acquired multicancer resistance to a plurality of different drugs. Nor is there any known prior art which correlates oncogene amplification and acquired resistance to chemotherapeutic cancer drugs.

The invention departs from the conventional focus upon specific gene-cancer-drug combinations to provide a procedure for the substantially concurrent determination of the presence or absence of drug resistance of a plurality of different cancers to an assortment of chemotherapeutic agents.

SUMMARY OF THE INVENTION

This invention provides a process for detecting acquired resistance to any chemotherapeutic agent by any type of human cancer cell. The process comprises assaying RNA from human cancer cells to determine whether the expression of at least one of a preselected spectrum of at least two, and preferably from about 3 to about 10, different genes is increased in comparison to a control. The control may, for example, be a gene included in the spectrum of genes but which is not amplified or expression of the relevant mRNA in either normal tissue or untreated tissue from the same patient tumor.

DESCRIPTION OF THE PREFERRED EMBODIMENTS

Figure 1:
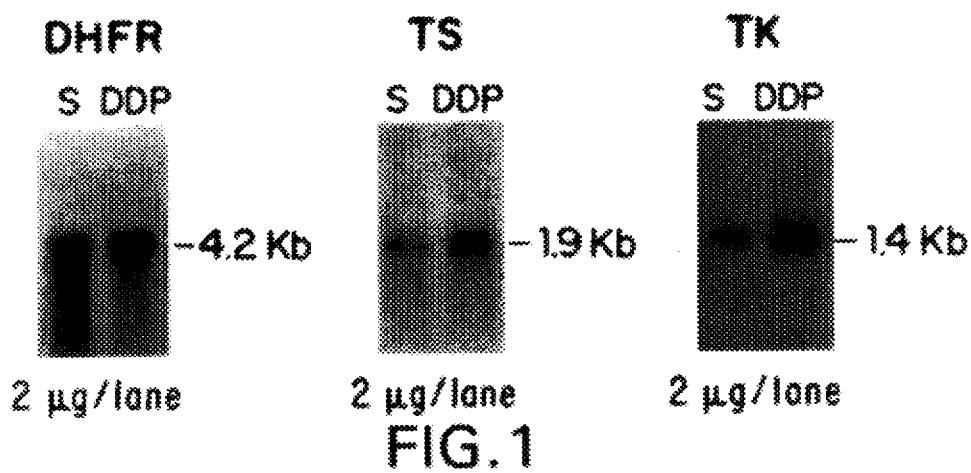
FIG. 1 is a Northern m-RNA analysis of the thymidylate synthase (TS) cycle genes (DHFR, TS and thymidine kinase (TK)) from a human colon carcinoma cell line HCT8 sensitive (S) and resistant (DDP) to cisplatin.
Figure 2:
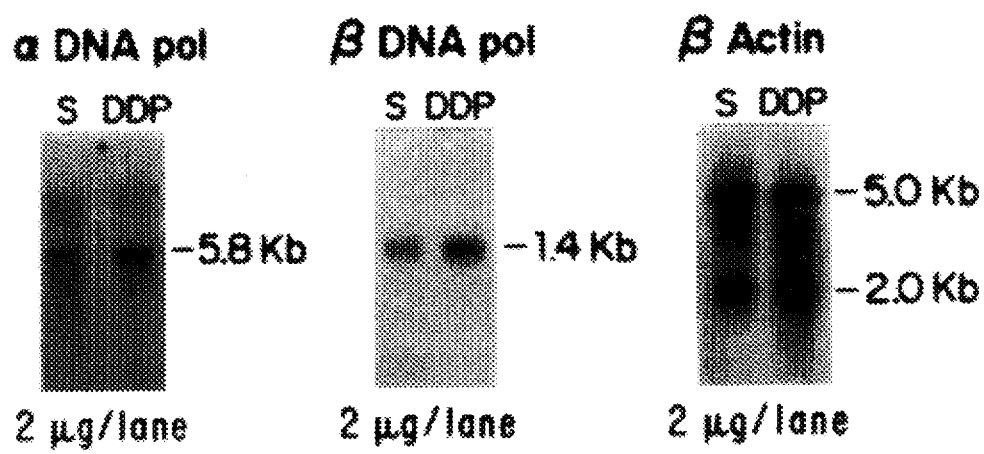
FIG. 2 is a Northern m-RNA analysis of the DNA repair enzyme genes (DNA polymerase α and DNA polymerase β from a human colon carcinoma cell line HCT8 sensitive (S) and resistant (DDP) to cisplatin and of β actin, a control.
Figure 3:
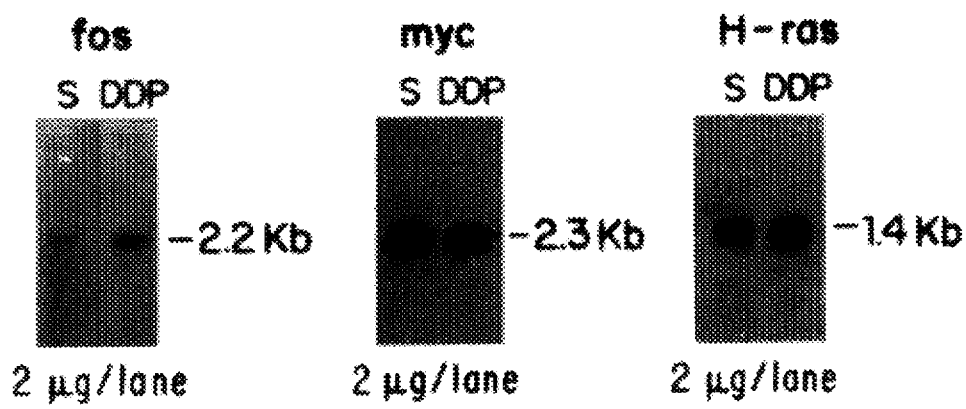
FIG. 3 is a Northern m-RNA analysis of the oncogenes (c-fos, H-ras and c-myc) from a human colon carcinoma cell line HCT8 sensitive (S) and resistant (DDP) to cisplatin.
Figure 4:
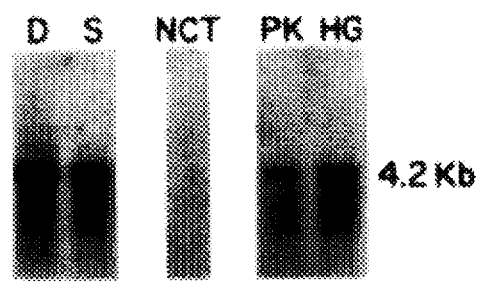
FIG. 4 is a Northern m-RNA analysis of the TS cycle genes (DHFR, TS and TK) from both in vitro CTSS (S) and HCT8DDP (D) cells, normal human colon tissue (NCT) and two patients (PK and HG) that have failed cisplatin treatment.
Figure 4:
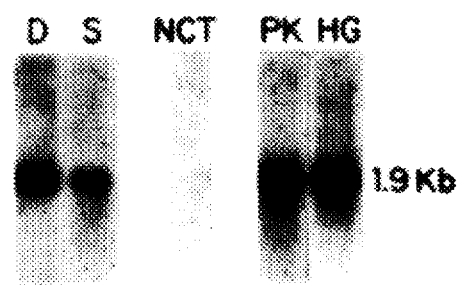
Figure 4:
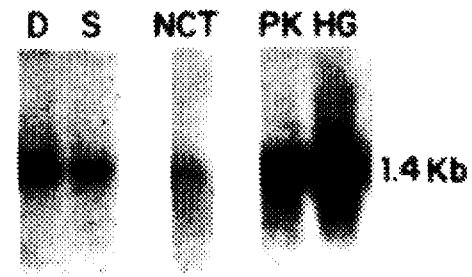

In each case, approximately $10^8$ cells in logarithmic growth phase were harvested for isolation. FIGS. 1–3 reflect in vitro data; FIG. 4 reflects data from patient tissue. Total RNA was extracted with guanidinium isothiocyanate and enriched for mRNA by oligo(dT)-cellulose column chromatography. The mRNA was denatured in 1M glyoxal and 50% dimethyl sulfoxide. Electrophoresis of mRNA samples on horizontal agarose gels with subsequent transfer onto Genatran nylon filters was performed as described.6/ The filters were hybridized to $^{32}$P-nick-translated DNA probes at 65° C. overnight in 6XSSPE, 7% SDS, 10% dextran sulfate, 0.5% rehydrated, powdered skim milk (Carnation, "blotto"). The hybridized filters were washed at room temperature for 10 min and twice at 37° C. for 10 min in 6XSSC/0.1% SDS, and exposed to Kodak X-Omat AR film with intensifying screens. Quantitation densitometry was performed by using a scanning densitometer as previously described.

6/ (1988) Scanlon, K. J., et al., Proc. Nat'l.Acad. Sci. 85:650.

FIG. 1—TS Cycle—The Northern blots show that the dihydrofolate reductase mRNA was 2.4 times higher in cells resistant to cisplatin (HCT8DDP) than in cells sensitive to cisplatin (HCT8S). The mRNA for dTMP synthase was increased 4.2-fold in HCT8DDP cells as compared with that from HCT8S. The mRNA for thymidine kinase was 3.5 fold higher in the resistant cells.

FIG. 2—DNA Repair Genes—depicts the expression of the DNA polymerase genes, mRNA from HCT8S and HCT8DDP cells as analyzed by Northern blot. As comparison with the β actin control indicates, a 2-3 fold overexpression of DNA polymerase α and β genes in the resistant HCT8DDP cell line is apparent as compared with the sensitive HCT8S cell line.

FIG. 3—Oncogenes—shows that the mRNA level of c-fos and c-H-ras genes increased in the resistant HCT8DDP cells. However, the expression of the mRNA of the c-myc gene was similar in the sensitive and resistant cells.

FIG. 4—Analysis of RNA Human TS Cycle Colon Genes—This figure depicts gene expression of HCT8S (S) and HCT8DDP (D) cells, normal colon tissue (NCT) and two patients (PK and HG) that failed chemotherapy with cisplatin upon analyses for changes in expression by the DHFR, thymidylate synthase (TS) and thymidine kinase (TK) genes. NCT had the lowest amount of mRNA for all three genes. The two patients that failed cisplatin chemotherapy have the highest amount of RNA for TS and TK genes. HCT8DDP cells have a consistently higher amount of mRNA for all three genes studied when compared to HCT8S cells.

FIGS. 5–8 depict Southern analysis from five types of human cancer for changes in the DNA polymerase β gene.

High molecular weight cellular DNA was extracted from the HCT8 cells, utilizing sequential treatments of proteinase K and ribonuclease A, phenol/chloroform extraction, and ethanol precipitation. DNA samples were quantitated on a DNA fluorometer (Hoefer Scientific) and digested with the appropriate restriction endonuclease in standard conditions recommended by the supplier (BRL). The fragments were separated by electrophoresis on a 0.8% agarose gel, denatured and transferred onto Zeta-Probe filters as previously described.7/ Hybridization and washing conditions were the same as for RNA blot.

7/ (1988) Scanlon, K. J., supra.

Figure 5A:
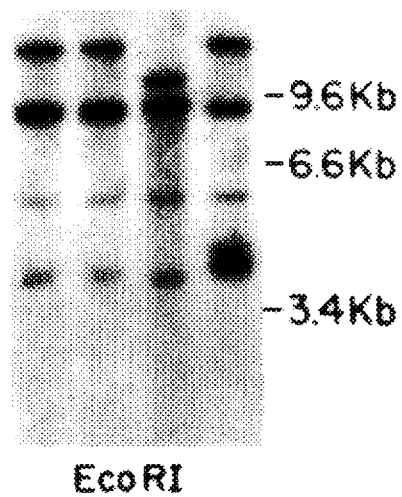
FIG. 5a is a Southern DNA analysis of the DNA polymerase β gene in the in vitro cell line HCT8S (S) and HCTSDDP (D), normal human colon tissue (N) and a patient (PK) that failed cisplatin/5 fluorouracil chemotherapy.

FIG. 5a depicts a comparison of DNA for the DNA polymerase β gene to a human colon carcinoma cell line HCT8 sensitive (S), a human colon carcinoma cell line HCT8 resistant to cisplatin (D), normal colon tissue (N) and colon tissue from a patient (PK) that failed cisplatin and 5 fluorouracil chemotherapy. The normal tissue has a different pattern from the carcinoma cells as evidenced by the appearance of a band at a 5.5 Kb when compared to normal tissue.

Figure 5B:
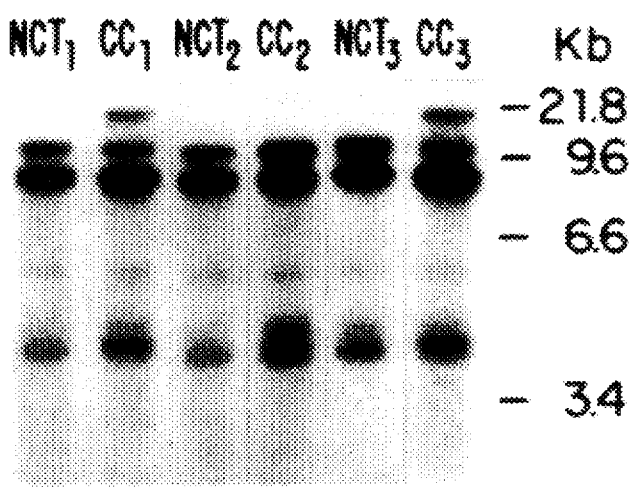
FIG. 5b is a Southern DNA analysis of the DNA polymerase β gene in three patients with colon carcinoma (untreated $CC_{1-3}$) and their corresponding normal colon tissue ($NCT_{1-3}$).

FIG. 5b depicts changes in the DNA polymerase β gene for three normal colon tissue samples ($NCT_{1-3}$) and three colon carcinoma tissue samples ($CC_{1-3}$).

Figure 6:
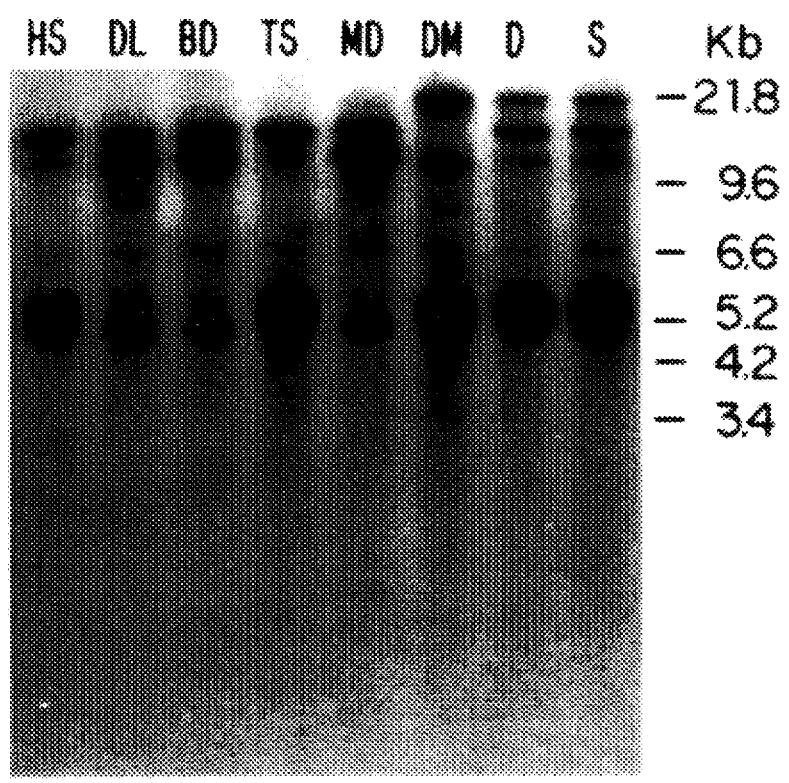
FIG. 6 is a Southern DNA analysis of the DNA polymerase β gene in six ovarian patients (DM, MD, TS, BD, DL and HS) and an in vitro human ovarian cell line A2780 sensitive (S) and resistant (D) to cisplatin.

FIG. 6 shows that tissue from five ovarian patients (patients DM, MD, TS, BD and DL) treated with cisplatin in combination with 5 fluorouracil or cytoxane (patient HS) lost a high molecular weight band (20 Kb) upon development of resistance to chemotherapy in all except patient DM. DM may have had only a partial relapse. A low molecular weight band (5.5 Kb) was lost in 3 of the 6 drug resistant patients. These data strongly suggest change in the DNA polymerase β gene in response to chemotherapy.

Figure 7:
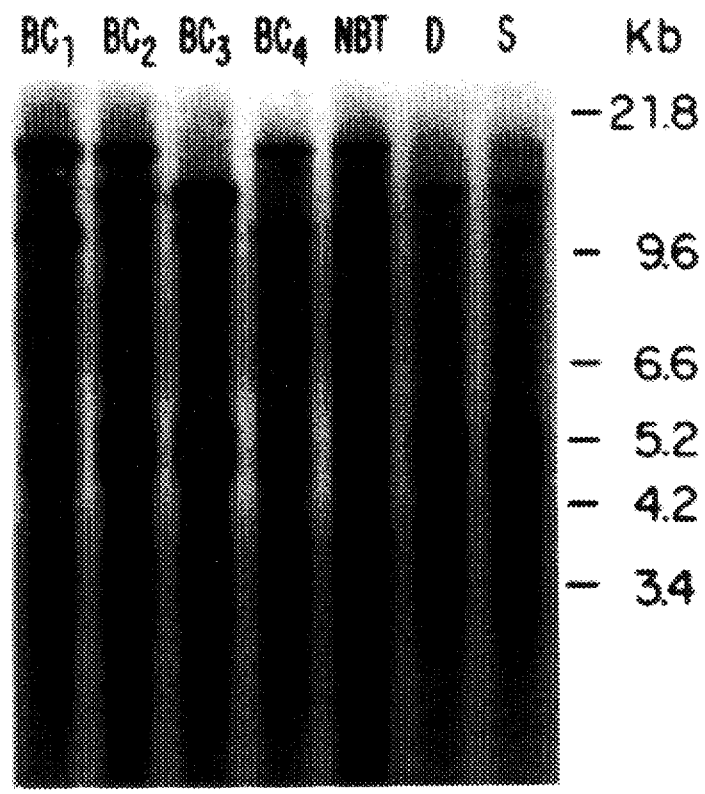
FIG. 7 is a Southern DNA analysis of the DNA polymerase β gene in four human breast carcinoma patients ($BC_1$, $BC_2$, $BC_3$ and $BC_4$), one normal human breast tissue sample (NBT) corresponding to patient $BC_4$, and an in vitro human breast carcinoma cell line MCF7 sensitive (S) and resistant (D) to cisplatin.

FIG. 7 shows that tissue from four breast carcinoma patients is characterized by an additional band at 5.2 Kb and at 5.5 Kb $BC_{1-4}$. Tissue from three of the four patients ($BC_{1-3}$) yielded an additional band at 5.5 Kb. These 5.2 Kb bands appear to offer a marker to discriminate normal from neoplastic tissue.

Figure 8:
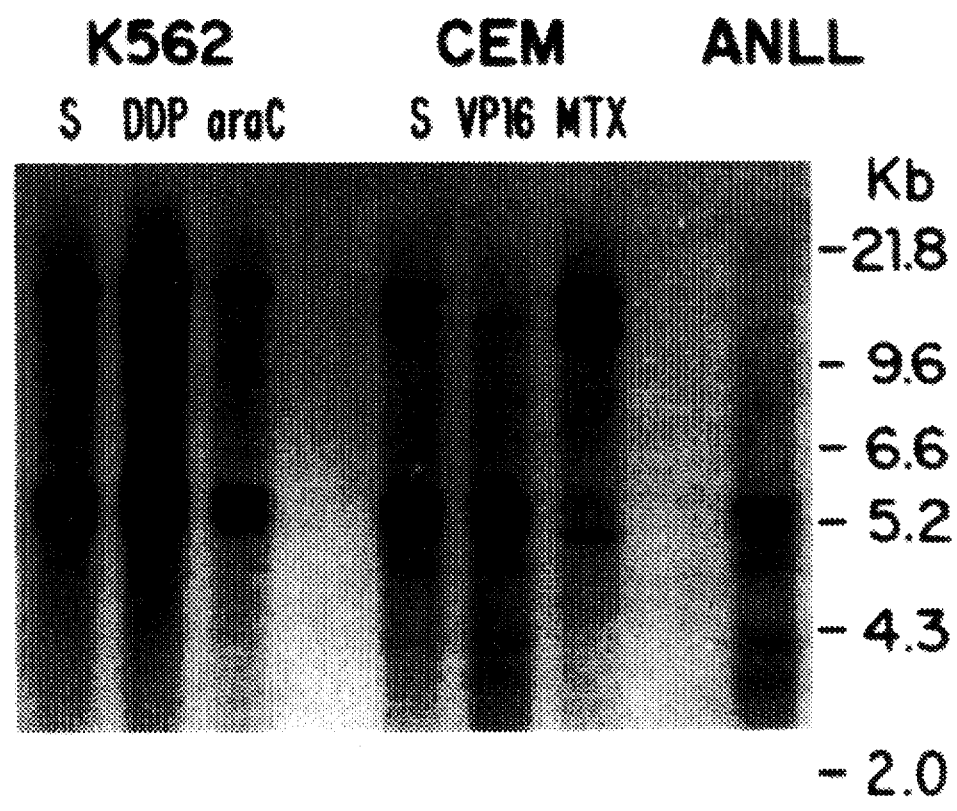
FIG. 8 is a Southern DNA analysis of the DNA polymerase β gene in one patient with acute non-lymphocytic leukemia (ANLL) and two human leukemia cell lines K562 (chronic myleocyctic leukemia) and CEM (T cell leukemia) resistant to cisplatin (DDP) or cytosine arabinoside (araC) or etoposide (VP16) or methotrexate (MTX).

FIG. 8 shows that Southern analysis of human leukemia cells resistant to cisplatin (DDP), VP16 or MTX yield additional bands at about 15 Kb. These band changes appear to provide markers for drug resistance in neoplastic cells, including human leukemia cells.

In some tumors, only enhanced gene expression in the absence of gene amplification has been demonstrated for drug resistance. Most importantly, the use of RNA permits extension of the concept of gene amplification upon drug resistance to the messenger level, a phenomenon previously not amenable to investigation due to the inordinate number of patient cells required for RNA analysis. The polymerase chain reaction assay circumvents that requirement. The use of as little as 100 ng total patient RNA is sufficient to generate a strong signal after completion of 25 rounds of amplification.

Figure 9:
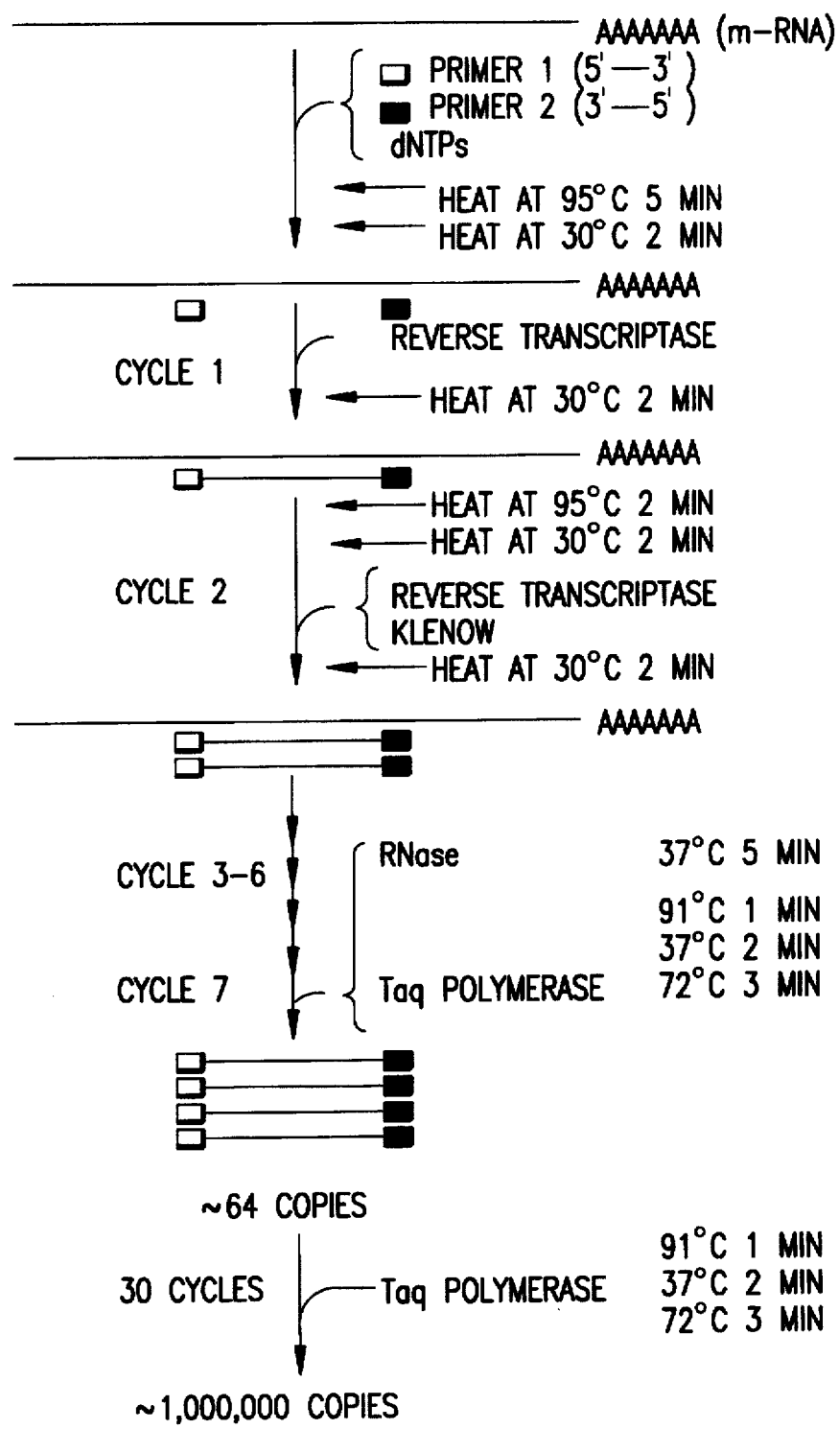
FIG. 9 is a flow chart depicting the steps of the assay of the invention.

A schematic diagram outlining the steps of the assay useful in the invention is shown in FIG. 9. This assay requires two converging, preferably about twenty base, oligoprimers oriented in opposite directions, for the 5' and 3' ends of the gene sequence to be analyzed. These oligoprimers may be synthesized by conventional methods.

Figure 10A:
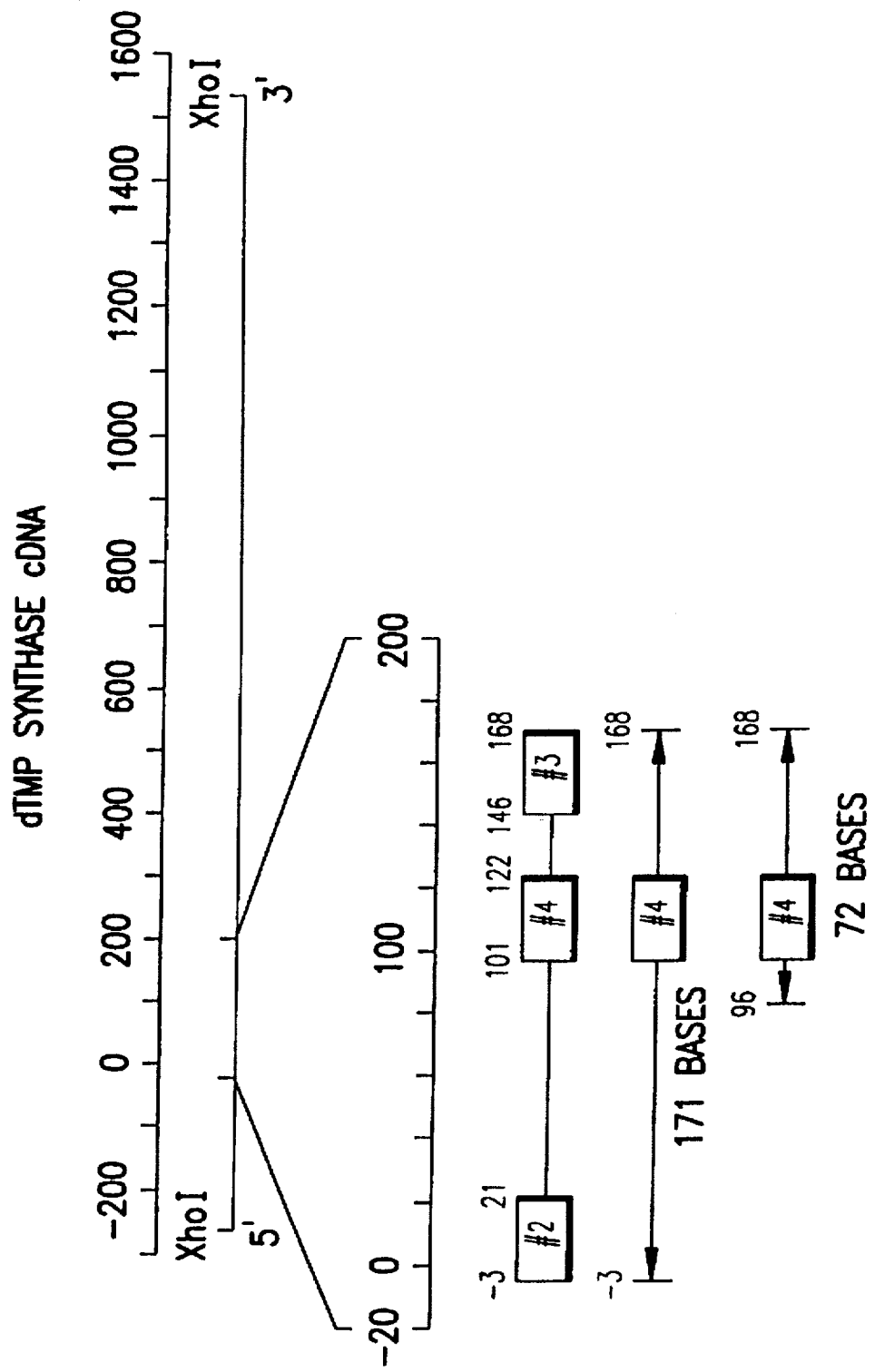
FIG. 10a depicts the oligoprimers for dTMP synthase.
Figure 10B:
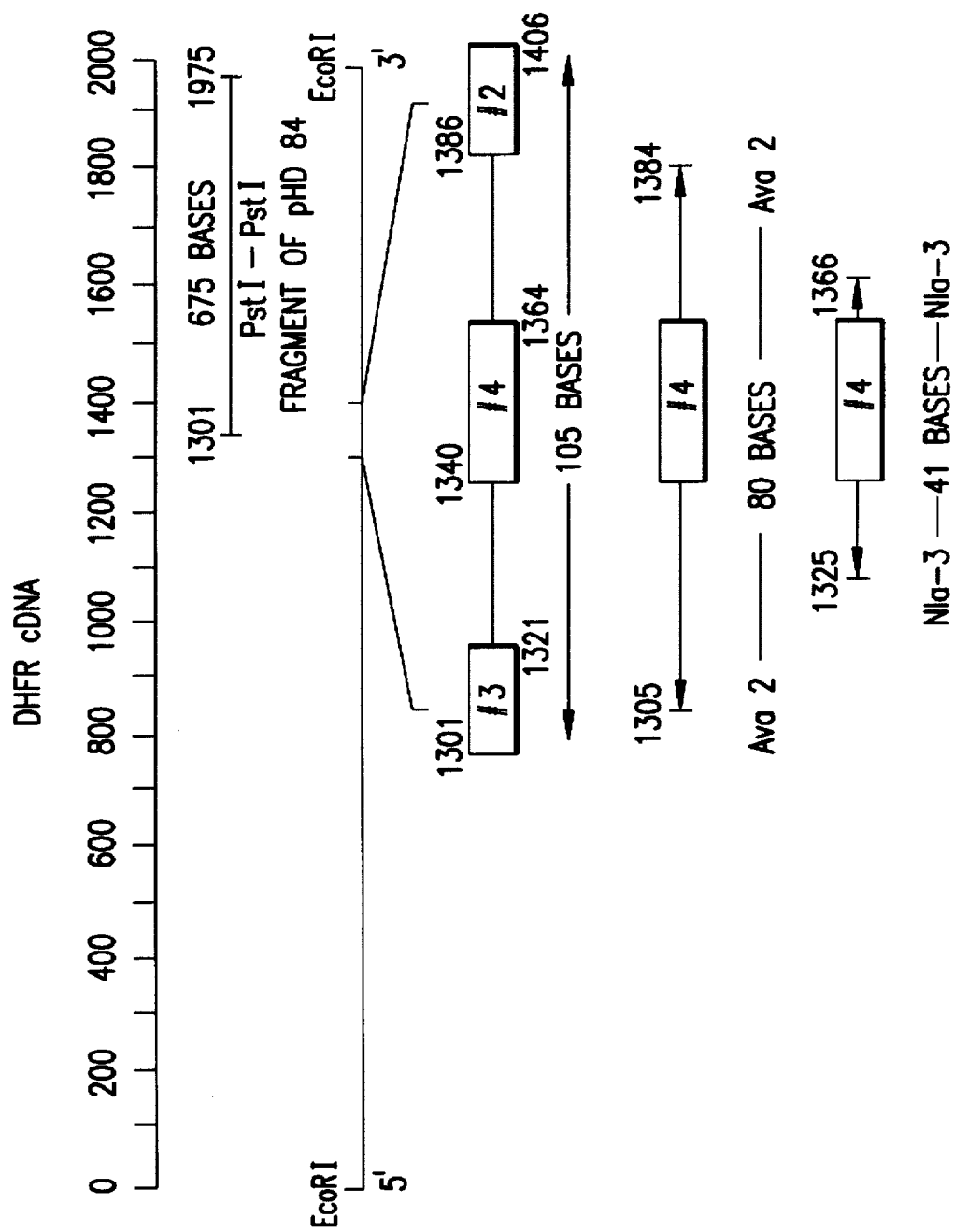
FIG. 10b depicts the oligoprimers for DHFR.

The oligoprimers for dTMP synthase are shown in FIG. 10a; the oligoprimers for DHFR are shown in FIG. 10b. More specifically for dTMP synthase, TS-2 is the 3'-5' oligoprimer complementary to DNA (bases -3–21) having the sequence GCC ATG CCT GTG GCC GGC TCG GAG, and TS-3 is the 5'-3' primer complementary to mRNA (bases 146–167) having the sequence AGG GTG CCG GTG CCC GTG CGG T. The probe for identifying the TS sequence (bases 101–122) is denoted TS-4 and has the sequence AGG ATG TGT TGG ATC TGC CCC A. There is a PstI restriction enzyme site in this sequence.

DHFR-2 is the 3'-5' oligoprimer complementary to DNA (bases 1271–1291) having the sequence GAC CGC GCG TTC TGC TGT AAC. DHFR-1 is the 5'-3' oligoprimer complementary to mRNA (bases 1386–1406) having the sequence GAG CGG TGG CCA GGG CAG GTC. The probe for identifying the sequence, DHFR-3, has the sequence ACA GCA GCG GGA GGA CCT CCG AGC. There is an Ava II restriction enzyme site in this sequence.

Figure 10C:
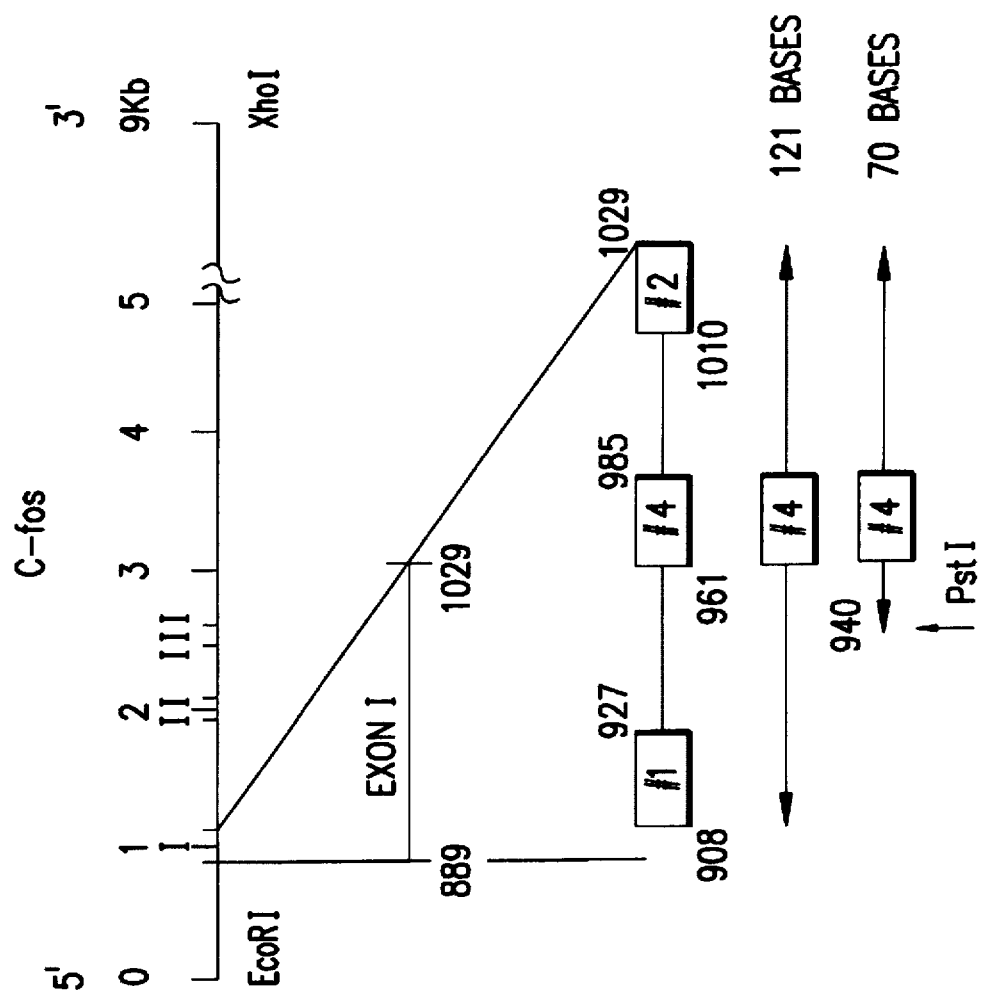
FIG. 10c depicts the oligoprimers for c-fos.

FIG. 10c—cfos$^{-2}$ is the 5'-3' oligoprimer complementary to DNA (exon 1, 409–429) having a sequence CTG CGC GTT GAC AGG CGA GC. C-fos-3 is the 5'-3' oligoprimer complementary to m-RNA (exon 1, 307–326) having a sequence ACG CAG ACT ACG AGG CGT CA. The probe for identifying the sequence is cfos-4, and has the sequence TGA GTG GTA GTA AGA GAG GCT ATC. There is a Pst I restriction enzyme site in this sequence.

Figure 10D:
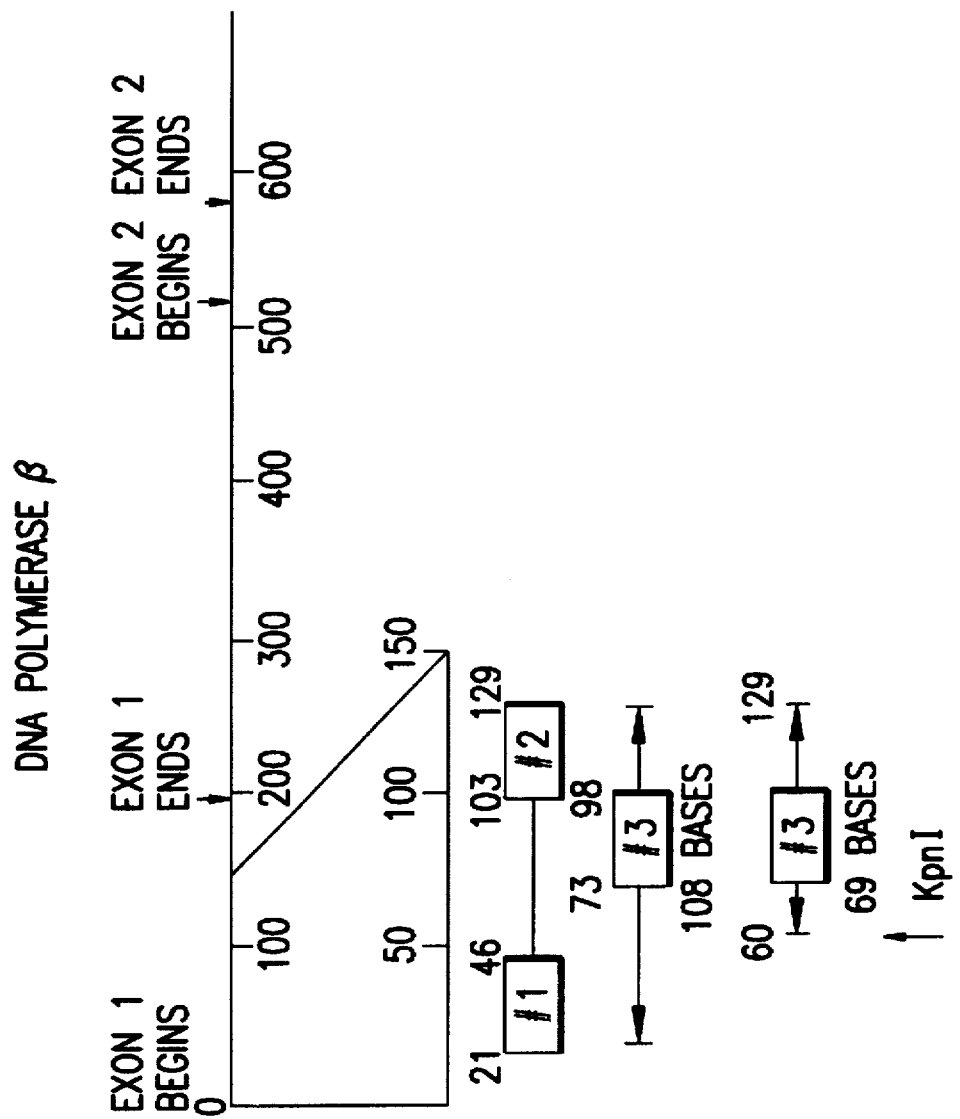
FIG. 10d depicts the oligoprimers for DNA polymerase β.

FIG. 10d—DNA polymerase β-1 is the 5'-3' oligoprimer complementary to DNA (exon 1, 1–25) having a sequence of GGA GCT GGG TTG CTC CTG CTC CCG T. DNA polymerase β-2 is 5'-3' oligoprimer complementary to m-RNA (exon 1 103–129) having a sequence GCC TTC CGT TTG CTC ATG GCG GCC T. The probe for identifying the sequence is DNA polymerase β-3 and has a sequence ACC AGG GAC TAG AGC CCT CTC CCA G. There is a KpnI restriction enzyme site in this sequence.

Figure 10E:
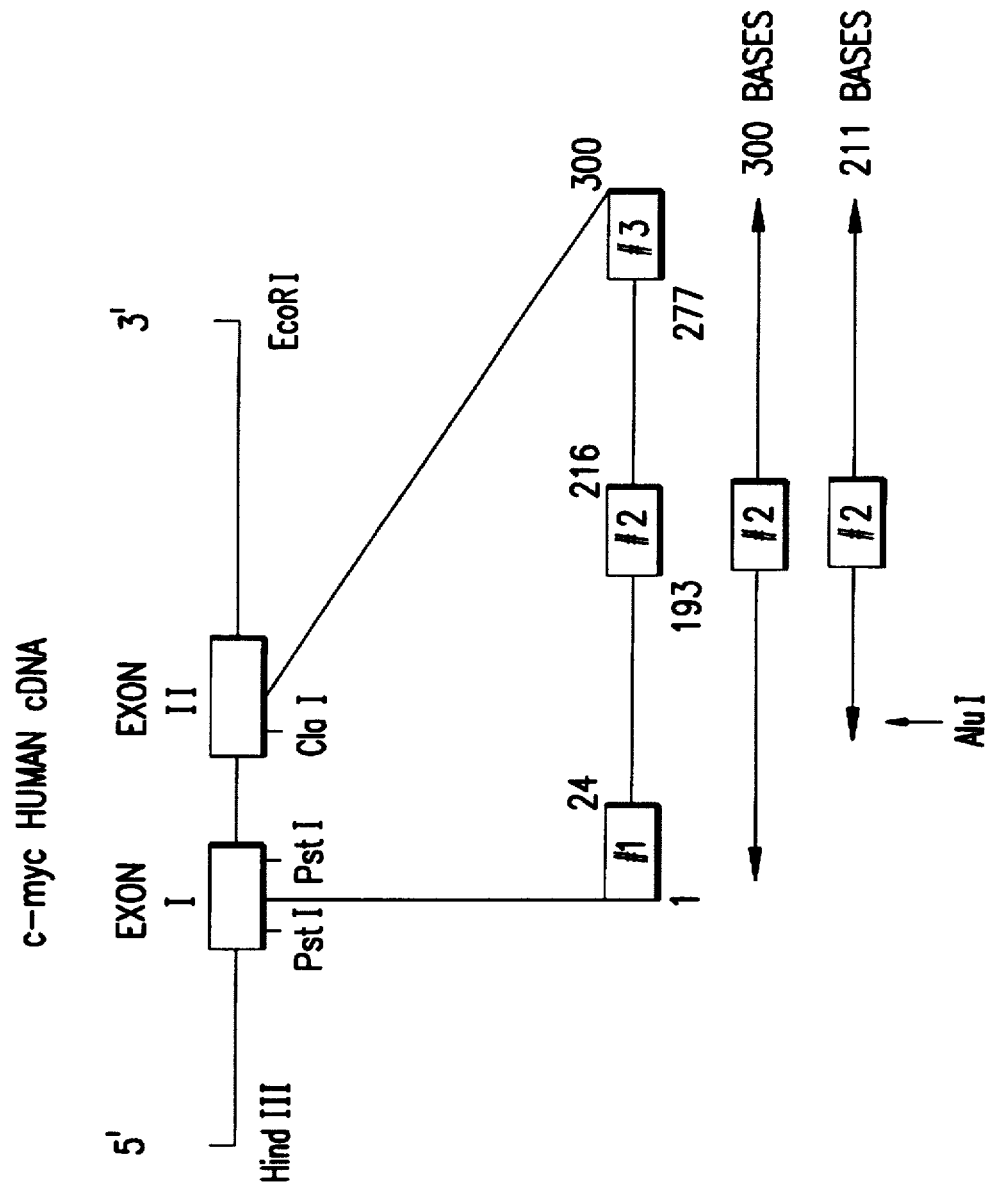
FIG. 10e depicts the oligoprimers for c-myc.

FIG. 10e—c-myc-1 is a 5'-3' oligoprimer complementary to either DNA or RNA (exon 1, 39–63) having a sequence of TCC AGC TTG TAC CTG CAG GAT CTG. c-myc-2 is the 5'-3' oligoprimer complementary to DNA or a probe for RNA (exon 2, 276–300) has a sequence CGG TGT CTC CTC ATG GAG CAC CAG. The probe for identifying the DNA sequence is c-myc-4 and has a sequence of GAC CAC CGA GGG GTC GAT GCA CTC T. The c-myc-3 is a 5'-3' oligoprimer complementary to only RNA (exon 2, 90–113) having a sequence AGG AGC CTG CCT CTT TTC CAC AGA. There is an AluI restriction enzyme site in the DNA/RNA sequence.

In the following examples the nucleic acid sequence of human dTMP synthase was amplified according to the assay of the invention.

EXAMPLE 1

Total RNA from both A2780 cells and patient cells (PK, HG, TMS, DM and MD) (FIG. 9) was incubated in 1× amplification buffer (19 mM tris-HCl pH 8, 6.6 mM MgCl$_2$, 100 pmoles of TS primer #2 and TS primer #3 (FIG. 10a), 6.0 mM β-mercapto-ethanol, 60 mM NaCl), 1 mM dithiothreitol (DTT) and 1.5 mM dNTPs (Pharmacia) in a final volume of 0.1 ml (FIG. 9). The Mg++ should be titrated for the optimum enzyme activity (1.5 mM). Samples were heated to 95° C. for 5 min. and cooled to 37° C. for 2 min., at which time 2 units of AMV reverse transcriptase (RT, Life Sciences) were added and incubated for an additional 2 minutes. Samples (1 µg of DNA or 100 ng of total RNA) were denatured and cooled again, and in round 2 both RT and 0.5 units Klenow DNA Polymerase (New England Biolabs) were added, followed by a 2 min. incubation (37°). In round 3, samples were heated to 95° C. for 2 min. Reverse transcriptase treatment was discontinued after two rounds, and additional 0.5 units DNA Pol were included in rounds 10 and 20. In round 3, 0.09 µg RNase A (Sigma) degraded the RNA following the denaturation step. In round 3, samples were heated to 95° (2 min.) and cooled to 72° for 3 min. This cycle of heating, annealing, and polymerization was continued for 25 rounds with 0.5 units of *Thermus aquaticus* DNA polymerase (Taq polymerase) (New England Biolabs). The calculated error rate for DNA pol is 1 in 5000 bases and higher temperatures minimizes mispriming (unpublished data). All enzymes were diluted in 1× amplification buffer+1 mM DTT. The polymerization time was increased with increasing number of cycles (i.e., from 1.5–3.0 min; from 10–25 cycles). After completion of the last round, samples were stored at 4° C. and electrophoresed in 1.8% agarose (0.5×TAE), transferred to Zeta Probe filters (BioRad) using the Vacublot apparatus (American Bionetics) in 0.4N NaOH, 30 min. TS #4, used as the probe to detect the amplified segment, was end-labeled by preparing a solution containing 20 units T4 kinase (Bethesda Research Laboratories, BRL), 40 pmoles oligonucleotide #4, 1× kinase buffer (7 mM tris-HCl, pH 7.5, 1 mM MgCl$_2$, 0.5 mM DTT), and 100 pmoles $^{32}$P-ATP and by incubating at 37°, 30 min. The labeled oligonucleotide was purified by running the incubation mixture on a DE-52 cellulose column. Prehybridizations were omitted, and filters were hybridized at 65° overnight in 20 ml 6XSSPE, 7% SDS, 10% dextran sulfate, 0.5% rehydrated, powdered skim milk [(Carnation) "blotto"], and 3×10$^8$ cpm radiolabeled TS #4 in a shaking water bath. The hybridized filters were washed three times in 6XSSC, 0.1% at 65°, 10 min. and autoradiographed at −70° on Kodak X-omat AR film. When desired, the amplified DNA (1 ul) was cleaved with 100 units Pst I (BRL) in the presence of 1× reaction buffer (50 mM Tris-HCl pH 8.0, 10 mM MgCl$_2$, 50 mM NaCl) and 0.1 mg/ml BSA for 1 hr. at 37°.

As stated above, performing each cycle of the assay of this invention produced one new single strand DNA molecule, which in this example was the 171 base dTMP synthase DNA. The single strand DNA molecules that were produced by the assay of this invention acted as templates for one or the other of the oligonucleotide primers during subsequent cycles of the assay. Extension of these oligonucleotides by Taq polymerase produced molecules of dTMP synthase that were 171 bases long. As a result, a chain reaction was sustained which resulted in the accumulation of, in this instance, the specific 171-base pair double stranded DNA at an exponential rate as compared to the number of cycles of the assay performed (FIG. 9).

EXAMPLE 2

The assay reaction described in Example 1 was carried out four different times, each reaction starting with 1 µg of dTMP synthase mRNA and one pair of oligoprimers comprised of the four different oligoprimers for the 171 base pair dTMP synthase fragment as illustrated in FIG. 10a. The four pairs of oligoprimers used were: TS-1 and TS-3; TS-2 and TS-3; TS-1 and TS-4; and TS-2 and TS-4.

To test the four different amplification products obtained, TS-4 probe labeled with $^{32}$P was hybridized to the products and analyzed by Southern blot.

Only oligoprimers TS-2 and TS-3 optimally amplified the dTMP synthase gene fragment, as indicated by a band corresponding to 169 bases on the Southern blot. Oligoprimers TS-2 and TS-4 amplified the sequence to a lesser extent, while the combinations of primers TS-1 and TS-3, and TS-1 and TS-4 were not successful. The selection of oligoprimers for a given gene sequence that is to be amplified by the assay of the invention is critical.

There was an exponential growth of the 171-base pair fragment which began with 1 µg of human dTMP synthase mRNA and TS-2 and TS-3 oligoprimers. After 10 cycles, the target sequence of dTMP synthase was greatly amplified. Amplifying 1 µg total human dTMP synthase mRNA produced approximately 5×10$^{-19}$ moles of the target sequence from one copy of gene and produced a 1,000,000-fold increase of this fragment after 20 cycles of the assay reaction.

In preparation for the modified PCR assay, tumor cells are obtained from patients' tissue or peritoneal fluid, and total RNA is isolated as described. With the use of oppositely oriented primers (designated as TS #2 and TS #3) a 171 bp region of the TS gene is replicated repeatedly in vitro, flanked by the two oligomers. FIG. 10a schematically portrays the position of the oligoprimers vis-a-vis the rest of the TS gene.

Experimentally, the oligomers are annealed to the RNA template (FIG. 9), and prime the first strand polymerization using reverse transcriptase. The samples then undergo cycles of denaturation, annealing, and polymerization by addition of heat-stable DNA Polymerase. This treatment is continued for 25 rounds, and inclusion of Ribonuclease A in round 3 helps eliminate RNA which may compete for oligonucleotide binding. RNA was used in this assay instead of DNA since the lower sequence complexity of RNA should enhance priming efficiency, and totally intact RNA is not required for successful enzymatic amplification since the target sequence of amplification is relatively short (171 bp).

Upon termination of the amplification reaction, the samples are electrophoresed in 0.5× TAE and alkaline blotted onto Zeta Probe filter membranes. The amplified DNA segment is detected by probing with a third oligomer (designated as TS #4) complementary to a region within the amplified sequence (FIG. 10a).

EXAMPLE 3

Figure 11A:
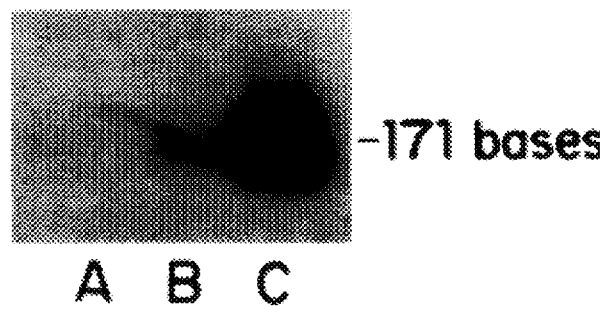
FIG. 11 show amplification of samples by the FIG. 9 assay. DNA product (10 μl) from A2780S RNA after 10, 15 and 20 rounds (Lanes A–C). Digestion of the amplified region with Pst I: Lane A, uncut product; Lane B, product digested with Pst I.
Figure 11B:
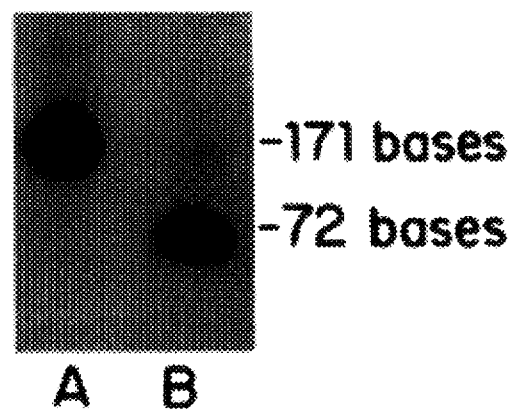

FIG. 11 essentially portrays control experiments demonstrating the successful adaptation of the assay using the modifications alluded to above. FIG. 11a detects the progressive exponential amplification of the desired 171-bp segment in A2780 cells between 10 and 20 rounds. The amplified fragment of A2780S m-RNA is not yet detected at the end of 10 rounds of the PCR assay (Lane A), but the 15-round sample does yield a noticeable band (Lane B), and marked amplification is observed upon completion of twenty rounds (Lane C). This product from the PCR assay was further identified as the defined sequence. As shown in FIG. 11b, the sequence to be amplified was selected so that it contained a cleavage site for a restriction endonuclease, in this case Pst I. The PCR product derived from 25 rounds of amplification was then subjected to Pst I digestion and probed with TS #4. Theoretically, such a treatment should cleave the amplified sequence into two fragments, only one of which (the 72-bp moiety) should be detected by autoradiograph (see FIG. 11b). FIG. 11b depicts the results of this digestion as a segment shorter in length than the 171-bp one hybridized to the radioactive probe.

EXAMPLE 4

Figure 12A:
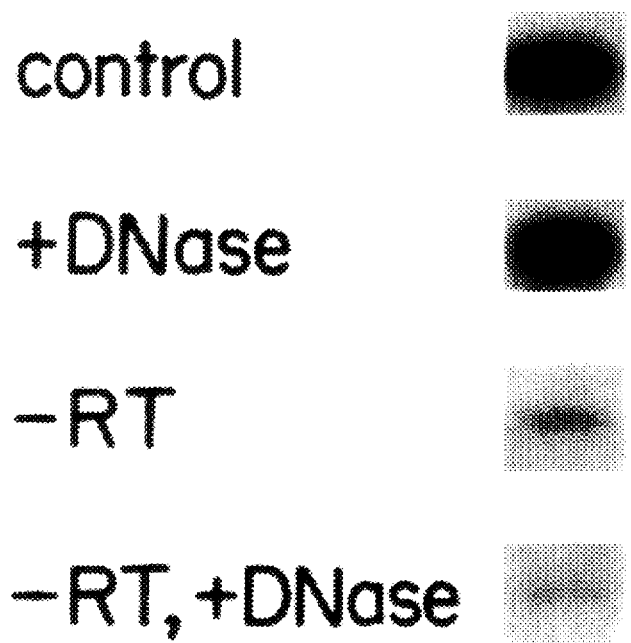
FIG. 12 depict analyses of the amplification product. The product assay for DNA contamination of mRNA samples. Shown are control, RNase free DNase treated (+DNase), minus reverse transcriptase (–RT), and minus reverse transcriptase and RNase free DNase treated (–RT, +DNase). Amplified product of 1, 10, 100, 1000 picograms (Lanes 1–4) of TS m-RNA derived from the BRL T7 RNA polymerase assay.
Figure 12B:
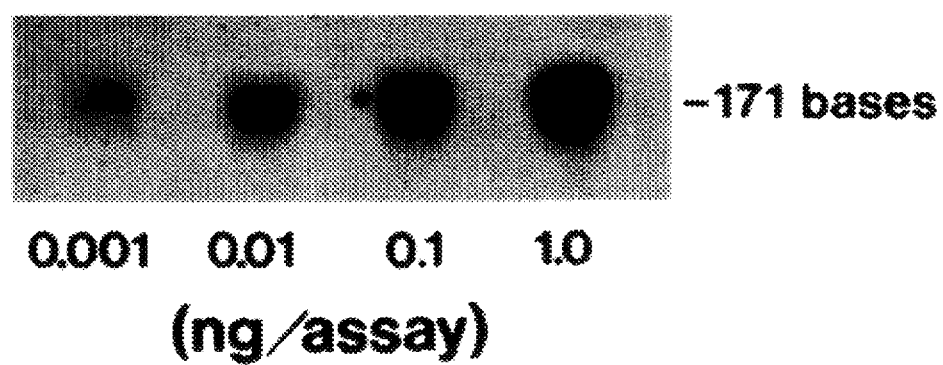

Before examining levels of TS m-RNA in drug-resistant cells, potential practical problems of the PCR assay must be considered. First, m-RNA degradation may affect the true amplification seen in the samples. However, an amplified sequence of only 171 bp will minimize the effect of m-RNA degradation. Defined concentrations of standard TS m-RNA are also run concurrently in the PCR assay for detection of any degradation. Secondly, DNA contamination of the samples may lead to amplification of TS DNA sequences as well as RNA (FIG. 12a). Amplification of the m-RNA sample in the absence of reverse transcriptase demonstrates a faint band suggesting possible DNA contaminations. Treatment with DNase (5 μg for 5 min) and removal of reverse transcriptase from the assay eliminates most of the DNA contamination. DNA contamination of the m-RNA samples was determined to be less than 0.1% of the sample. Finally, we examined the PCR assay for linearity of amplification using TS m-RNA generated from a pTZU18 (T7 RNA polymerase) vector (BRL) containing the TS cDNA. There was a linear increase in the product of transcription when different concentrations of TS m-RNA ranging from 1–1000 picograms were subjected to the PCR assay (FIG. 12b).

EXAMPLE 5

Figure 13:
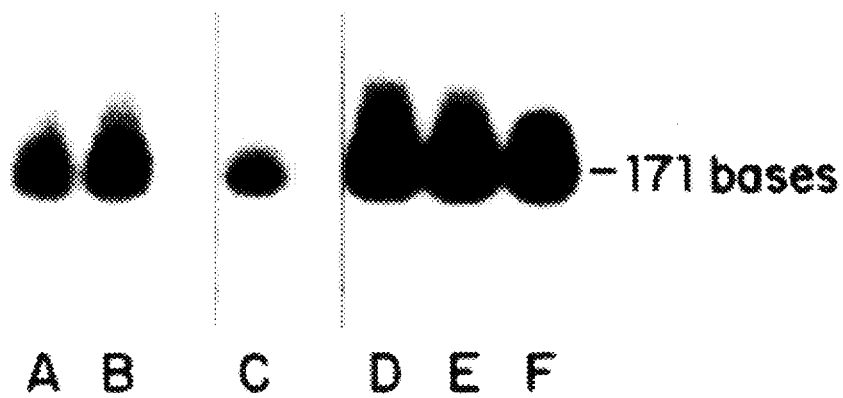
FIG. 13 shows amplified product with ovarian RNA from A2780S (Lane A), A2780DDP (Lane B), normal ovarian tissue (Lane C), MD (Lane D), DM (Lane E) and TMS (Lane F) cells after 25 rounds. The A2780 cells were maintained in culture as described. Amplified product from colon RNA from HCT8 (Lane A'), HCT8DDP (Lane B'), normal colon tissue (Lane C'), colon carcinoma (Lane D', E'), and colon carcinoma that failed treatment with cisplatin, PK (Lane F') and HG (Lane G').
Figure 13:
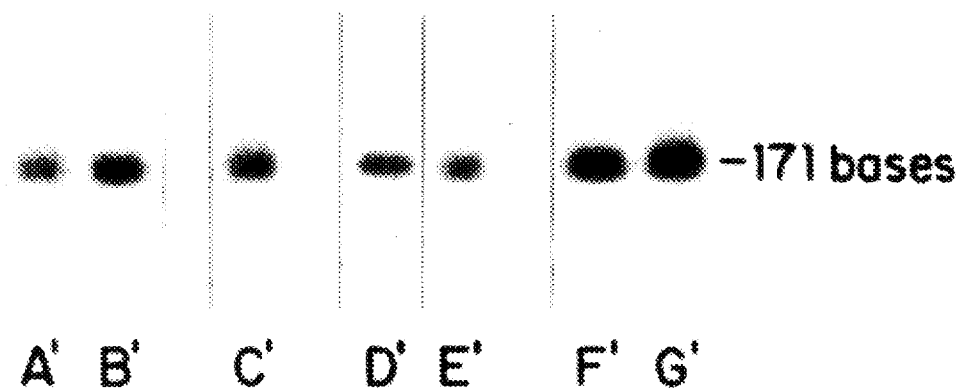

The next step concerns the examination of elevated TS gene expression upon resistance to cisplatin/5-FUra in six different ovarian tissue samples: the aforementioned A2780S ovarian cell line sensitive to cisplatin; a subline (termed A2780DDP) 3-fold resistant to cisplatin (FIG. 13; A,B); and tumor cells from three ovarian carcinoma (MD, DM and TMS) patients failing treatment with (and therefore resistant to) the cisplatin/5-FUra combination (FIG. 13; D,E,F). Previous work with the A2780DDP cells established a 3.6-fold enhancement of TS mRNA and enzyme activity (without gene amplification) as compared to the parent line. With respect to the ovarian tissue samples, resistance to the chemotherapeutic regimen correlated with a 4-fold amplification of m-RNA and DNA in the MD, DM and TMS samples. This information allows us to test the utility of the PCR assay as a method of detecting failure to chemotherapy, since a small degree of elevation in TS expression could be magnified and detected definitely after 25 rounds of the polymerization reaction. To this end, total RNA from all six samples was incubated with the oligoprimers in the PCR assay. The results, shown in FIG. 13A, point to a 3.8-fold difference in the PCR product of the A2780DDP cells as opposed to the A2780 cells. The ratio of in vitro enzymatic amplification was similar to that measured by northern blot analysis. The three patients (FIG. 13; D,E,F) MD, DM and TMS showed 9.6-, 9.0-, and 8.2-fold increased, respectively, in TS m-RNA when compared to normal ovarian tissue (NOT) (FIG. 13; C). The in vitro enzymatic amplification of RNA in the patient cells confirmed the previously described increase in TS gene expression. These results show that in the three patients, amplification of TS was not limited to the level of the gene, but that cells failing treatment with cisplatin/5FUra exhibit higher expression of TS m-RNA.

In human colon samples, the PCR product of HCT8DDP cells was 4.1-fold greater than the drug-sensitive HCT8S cells (FIG. 13; A', B'), which is similar to the difference found using Northern analysis. Normal colon tissue (FIG. 14; C) and human colon carcinoma tissue untreated with cancer chemotherapeutic agents (FIG. 13; D', E') contained similar amounts of TS m-RNA. In contrast, two colon carcinoma patients (PK and KG) who failed cisplatin treatment also had elevated TS m-RNA (3.7- and 9.6-fold increases, respectively; FIG. 13; F', G').

Amplification of RNA or DNA is shown by comparison of levels of TS in patients with known clinical resistance to cisplatin/5-FUra and reported gene amplification to two sublines of A2780 ovarian carcinoma cells sensitive and 3-fold resistant to cisplatin. Previous studies have shown a direct relationship between the amount of m-RNA and TS enzyme activity.

These results are consistent with previous findings that resistance to chemotherapeutic agents results in an increase in the amount of mRNA and gene expression of dTMP synthase, DHFR, and the H-ras, c-fos, and c-myc oncogenes in carcinoma cells. Therefore, by amplifying mRNA that codes for these enzymes or oncogenes from even one carcinoma cell of a patient, and comparing the amount of amplification product with a control such as DNA from white blood cells, a rapid and accurate diagnosis of a cancer patient's chemotherapy progress can be made.

For example, a patient's cells that normally contained molecules of m-RNA for one of the enumerated enzymes or oncogenes, but that later contained five molecules of the same m-RNA when the patient had become resistant to chemotherapeutic agents, the amount of "drug resistant" genes that would be amplified via the assay of this invention would be five times greater than the amount of amplified genes in the normal (control) cells. Further, if the results of FIG. 4 showing a large increase in the expression of the gene for dTMP synthase were from a cancer patient, it would be immediately apparent that the patient had become resistant to the chemotherapeutic agents being administered. The patient could then be switched to different chemotherapeutic agents. The progress of the patient under the new regimen could be similarly monitored by daily analysis of the patient's carcinoma cells according to the methods of the present invention.

This invention provides means to detect acquired resistance to chemotherapeutic agents of all kinds, including, for example, those listed in Table I by all types of solid tumors and hematologic neoplasms. Solid tumors to which the invention is applicable include, among others, brain and peripheral nervous system tumors, tumors of the eye, cancer of the head and neck, respiratory tract cancer, alimentary tract cancer, genitourinary tract cancer, gynecologic cancer, breast cancer, cancer of the skin, melanoma, soft tissue sarcomas, bone and cartilage tumors and childhood solid tumors. Hematologic neoplasms to which the invention is applicable include, among others, acute lymphoblastic leukemia, acute myelocytic leukemia, chronic myelocytic leukemia, chronic lymphocytic leukemia, Hodgkin's disease, non-Hodgkin's lymphomas, Burkitt's lymphoma, plasma cell neoplasms, polycythemia vera, and myelofibrosis and myeloid metaplasis.

TABLE I

CHEMOTHERAPEUTIC AGENTS USEFUL IN NEOPLASTIC DISEASE

| CLASS | TYPE OF AGENT | NONPROPRIETARY NAMES (OTHER NAMES) |
|---|---|---|
| Alkylating Agents | Nitrogen Mustards | Mechlorethamine ($HN_2$) Cyclophosphamide Melphalan (L-sarcolysin) Uracil mustard Chlorambucil |
|  | Ethylenimine Derivatives | Thiotepa (triethylenethiophosphoramide) |
|  | Alkyl Sulfonates | Busulfan |
|  | Nitrosoureas | Carmustine (BCNU) Lomustine (CCNU) Semustine (methyl-CCNU) Streptozocin (streptozotocon) |
| Antimetabolites | Folic Acid Analogs | Methotrexate (amethopterin) Fluorouracil (5-fluorouracil; 5-FU) |
|  | Pyrimidine Analogs | Cytarabine (cytosine arabinoside) |
| Natural Products | Antibiotics | Dactinomycin (actinomycin D) Daunorubicin (daunomycin; adriamyacin; rubidomycin) |
| Natural Products |  | Doxorubicin (Adriablastina) Bleomycin Mithramycin |

TABLE I-continued

CHEMOTHERAPEUTIC AGENTS USEFUL IN NEOPLASTIC DISEASE

| CLASS | TYPE OF AGENT | NONPROPRIETARY NAMES (OTHER NAMES) |
|---|---|---|
|  | Antibiotics | Mitomycin (mitomycin C) Etoposide VP-16 VM-26 |
|  | Platinum Coordi-Complexes | Cisplatin (cis-DDP) Cisplatin analogues |
|  | Substituted Urea | Hydroxyurea |

The neoplastic cells to be analyzed by the methods herein described can be obtained by biopsy in the case of solid tumors, or in the case of cancer of the blood, blood samples can be obtained.

The methods of this invention can be used on a daily or less frequent basis to detect a patient's early resistance to chemotherapeutic agents.

Properties that render human cancer cells resistant to chemotherapeutic drugs appear to enhance the sensitivity of the same cells to other drugs. For example, human leukemia cells resistant to cisplatin evidence enhanced sensitivity to didoxy cytidine. Similarly, human ovarian cancer cells resistant to cisplatin have been shown to demonstrate increased sensitivity to AZT.

Reference to FIGS. 5a, 5b, 6 and 7 will show that the DNA of DNA polymerase β is modified upon transformation of normal cells to malignant cells both in vitro and in vivo and sensitive to resistant cells. More particularly, malignant cells yield Southern analysis bands at about 5.5 and 21.8 Kb which bands are not present in the DNA polymerase β of normal cells. Thus, DNA modification imparts utility as a cancer marker gene to the DNA of DNA polymerase β.

It is apparent that the method of this invention is subject to automation, e.g., by presently available PCR machines, presently available devices for automated Southern analysis, and the like. Such instrumentation is readily designed on a scale for use in the office of private practitioners.

I claim:

1. A process for detecting human cancer cells which have acquired resistance to a chemotherapeutic agent which process comprises assaying RNA from said cells to determine whether there has been an increase in the expression of H-ras or c-fos oncogene in comparison to a control, said assaying including the steps of (i) measuring the expression of the mRNA H-ras or c-fos oncogene and of a control gene, and (ii) comparing the amount of said expression of H-ras or c-fos mRNA with the amount of mRNA expression of said control gene wherein an increase in the amount of the expression of H-ras or c-fos mRNA as compared with the amount of the mRNA expression of said control gene is indicative that said human cancer cells have acquired resistance to a chemotherapeutic agent.

2. The claim 1 process in which said chemotherapeutic agent is cisplatin, ara-c, adriamycin, methotrexate 5-fluorouracil or N-phosphonacetyl-L-aspartate (PALA).

3. The claim 1 or claim 2 process in which said human cancer cells are cells of solid tumors or of hematologic neoplasms.

4. A process for detecting human cancer cells which have acquired resistance to a chemotherapeutic agent comprising:

(a) measuring by Northern blot assay the mRNA expression of a c-fos or an H-ras oncogene in cisplatin resistant and cisplatin sensitive HCT8 cells; and (b) comparing the amount of mRNA expression of said oncogene in the resistant and in the sensitive cells wherein an increase in the mRNA expression of said oncogene in cisplatin resistant cells in comparison with the mRNA expression of said oncogene in the sensitive cells is indicative that said cells have acquired resistance to said chemotherapeutic agent.

5. A process for the concurrent determination of the presence of chemotherapeutic agent resistance of a plurality of different human cancers to a plurality of different chemotherapeutic agents said process comprising the steps of (i) concurrently assaying the amount of mRNA expressed by at least one of a preselected spectrum of at least two genes associated with said chemotherapeutic agent resistance and the amount of mRNA expressed by a control gene, said preselected spectrum of genes and said control gene having been treated with a plurality of different chemotherapeutic agents;

(ii) comparing the amount of mRNA expressed by each gene in said preselected spectrum with the amount of mRNA expressed by said control gene wherein an increase in the amount of mRNA expressed by a gene in said spectrum as compared with the amount of mRNA expressed by said control is indicative that each gene in said spectrum which shows a comparative increase in mRNA expression with respect to said control has acquired resistance to at least one of said plurality of chemotherapeutic agents.

6. The claim 5 process in which 3 to 10 different genes are included in said preselected spectrum of genes.

7. The claim 5 process in which said preselected spectrum of genes includes at least one DNA repair gene, at least one thymidylate synthase (TS) system gene or at least one oncogene.

8. The claim 5 process in which said plurality of chemotherapeutic agents includes two or more of cisplatin, Ara-c, Adriamycin methotrexate, 5-fluorouracil or PALA.

9. A process for detecting human cancer cells which have acquired resistance to a chemotherapeutic agent which comprises assaying mRNA from said cells to determine whether there has been an increase in the mRNA expression of the H-ras or the c-fos oncogene in comparison to the mRNA expression of a control.

10. The claim 9 process in which the control is mRNA expression by (i) normal tissue or (ii) untreated patient tumor tissue.

11. A process for detecting human cancer cells which have acquired resistance to a chemotherapeutic agent comprising:

(a) measuring the mRNA expression of a c-fos or an H-ras oncogene in cisplatin resistant and cisplatin sensitive cells; and (b) comparing the amount of mRNA expression of said oncogene in the resistant and in the sensitive cells, wherein an increase in the mRNA expression of said oncogene in cisplatin resistant cells in comparison with the mRNA expression of said oncogene in the sensitive cells is indicative that said cells have acquired resistance to said chemotherapeutic agent.

12. The claim 11 process in which said mRNA expression is measured by Northern blot assay or by polymerase chain reaction assay.

13. The claim 11 process in which said human cancer cells are human colon cancer, breast cancer, ovarian cancer, or leukemia cells.

14. The claim 5 process in which said preselected spectrum of genes includes at least one dihydrofolate reductase (DHFR), TS, thymidine kinase (TK), DNA polymerase α, DNA polymerase β, apurinic endonuclease, c-fos, or H-ras gene.

* * * * *

UNITED STATES PATENT AND TRADEMARK OFFICE
CERTIFICATE OF CORRECTION

PATENT NO. : 5,736,326
DATED : April 7, 1998
INVENTOR(S) : Kevin J. Scanlon

It is certified that error appears in the above-indentified patent and that said Letters Patent is hereby corrected as shown below:

On the Cover Page: In the title, "...CHEMO THERAPEUTIC..." should be -- ...CHEMOTHERAPEUTIC... --;
Col. 8, line 49, "14" should be -- 13 --;
In the Claims: Col. 10, line 50 (claim 1), "the expression of the mRNA" should be -- the mRNA expression of the --.

Signed and Sealed this

Fifth Day of January, 1999

Attest:

Attesting Officer

Acting Commissioner of Patents and Trademarks